United States Patent [19]

Tischler et al.

[11] Patent Number: 4,621,091

[45] Date of Patent: Nov. 4, 1986

[54] 3-HYDROXYBENZO[b]THIOPHENE-2-SULFIDE DERIVATIVES COMPOSITIONS, AND METHOD OF USE THEREFOR

[75] Inventors: Allan N. Tischler, Westfield; Thomas J. Lanza, Jr., Edison, both of N.J.

[73] Assignee: Merck & Co., Inc., Rahway, N.J.

[21] Appl. No.: 658,859

[22] Filed: Oct. 9, 1984

[51] Int. Cl.$^4$ .................. A61K 31/34; A61K 31/38; C07D 333/64; C07D 401/12

[52] U.S. Cl. .................. 514/337; 514/422; 514/433; 546/274; 548/525; 549/54

[58] Field of Search .............. 549/54, 466, 525; 548/527; 546/274, 284; 514/337, 342, 422, 424, 443, 445

[56] References Cited

U.S. PATENT DOCUMENTS 3,594,478 7/1971 Brandstrom et al. ............... 549/54

OTHER PUBLICATIONS

Goodman et al, *The Pharmaceutical Basis of Therapeutics*, Sixth Ed., Macmillan Publ. co., New York, NY 1980, pp. 28 and 33.

*Primary Examiner*—Henry R. Jiles
*Assistant Examiner*—J. G. Mullins
*Attorney, Agent, or Firm*—Theresa Y. Cheng; Michael C. Sudol

[57] ABSTRACT

3-hydroxybenzo[b]thiophene-2-sulfide derivatives have been prepared by ring closure of an appropriately substituted 2—$R^1SCH_2S$— benzoic acid ester in the presence of a strong base. These compounds have been found to be specific inhibitors of 5-lipoxygenase and thereby useful in the treatment of inflammation, pain and fever associated with inflammation, arthritic conditions, asthma, allergic disorders such as allergic rhinitis and chronic bronchitis, skin diseases like psoriasis and atopic exzema, cardiovascular or vascular disorders, and other leukotriene mediated diseases. Furthermore, these compounds have been found to exhibit cytoprotective activity which does not involve the inhibition of gastric acid secretion but can be used at relatively low dosages for increasing the resistance of gastro-intestinal mucosa to strong irritants.

9 Claims, No Drawings

3-HYDROXYBENZO[b]THIOPHENE-2-SULFIDE DERIVATIVES COMPOSITIONS, AND METHOD OF USE THEREFOR

BACKGROUND OF THE INVENTION

This invention relates to benzothiophenes, particularly 3-hydroxybenzothiophenes having the 2-sulfide side chains, for example,

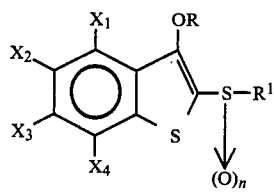

These novel benzothiophenes are found to be effective and specific 5-lipoxygenase inhibitors and are therefore useful in the treatment of leukotriene mediated diseases. Furthermore, they are found to be useful as cytoprotective agents.

Among various potent biological mediators derived from the oxygenation of arachidonic acid, prostaglandins and leukotrienes have been linked to various diseases. Notably, the biosynthesis of leukotrienes has been connected to immediate hypersensitivity reactions and pro-inflammatory effects.

It has been established that arachidonic acid undergoes oxygenation via two major enzymatic pathways:

(1) The pathway catalyzed by the enzyme cyclooxygenase; and (2) The pathway catalyzed by the enzyme 5-lipoxygenase.

Interruption of these pathways by enzyme inhibition has been explored for effective therapy. For example, non-steroidal anti-inflammatory drugs (NSAID) such as indomethacin and diflunisal are known cyclooxygenase inhibitors which inhibit the process wherein arachidonic acid is oxidized via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, *Science*, 220, 568 (1983); D. Bailey et al, *Ann. Rpts. Med. Chem.*, 17, 203 (1982)).

With respect to the cytoprotective activity of the compounds of the present invention, it has been known that (1) gastric cytoprotection does not involve inhibition of gastric acid secretion. For example, protaglandin F2B does not inhibit gastric acid secretion, but it does induce gastric cytoprotection (S. Szabo et al., *Experimentia*, 38, 254, 1982); (2) lower effective dosages of cytoprotective agents are required than that of gastric acid inhibitors; (3) it has been observed that specific 5-lipoxygenase inhibitors may also be effective cytoprotective agents; and (4) the cytoprotective activity of a compound may be observed in both animals and man by noting the increased resistance of gastrointestinal mucosa to strong irritants. For example, animal studies have shown that cytoprotective compounds will prevent gastric lesions induced by oral administration of strong acids, strong bases, ethanol, hypertonic saline, etc.

DETAILED DESCRIPTION OF THE INVENTION

A. Scope of the Invention

The present invention relates to novel compounds of formula (I):

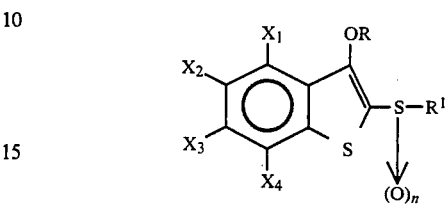

or a pharmaceutically acceptable salt thereof wherein $R^1$ and R independently are:

(a) H;

(b) loweralkyl, especially $C_{1-6}$ alkyl such as methyl, ethyl, i-propyl, n-propyl, t-butyl, n-butyl, i-pentyl, n-pentyl and n-hexyl;

(c) aryl especially $C_{6-14}$ aryl e.g., naphthyl, anthryl, phenyl or substituted phenyl of formula

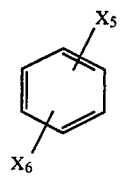

wherein $X_5$ and $X_6$ independently are:

(1) Q, where Q is H, loweralkyl especially $C_{1-16}$ alkyl, haloloweralkyl especially fluoro or chloro $C_{1-6}$ alkyl such as trifluoromethyl, phenyl or substituted phenyl, or naphthyl;

(2) halo especially chloro, fluoro, bromo or iodo;

(3) loweralkenyl especially $C_{2-6}$ alkenyl such as ethenyl and allyl;

(4) loweralkynyl especially $C_{2-6}$ alkynyl, for example, ethynyl or n-butynyl;

(5) —SQ;

(6) —OQ;

(7) —CHQCOQ$^1$, where Q is $Q^1$ and can be the same as or different from $Q^1$;

(8) —CHQCOOQ$^1$;

(10) —CH$_2$SQ or —CHQSQ$^1$;

(11) —CH$_2$OQ or —CHQOQ$^1$;

(12) —COQ;

(13) —COOQ;

(14) —OCOQ;

(15) —NQQ$^1$;

(16) —NQCOQ$^1$;

(17) —NQ(OQ$^1$);

(18) —NQ(SO$^1$);

(19) —NQSO$_2$Q$^1$;

(20) —SO$_2$NQQ$^1$;

(21) —SOQ;

(22) —SO$_2$Q;

(23) —SO$_3$Q;

(24) —CN;

(25) —NO$_2$;

(26) —CONQQ$^1$);

(27) —NO;

(28) —CSQ;
(29) —CSNQQ¹;
(30) —CF₂SQ;
(31) —CF₂OQ;
(32) —NQCONHQ¹ or NQCONQ¹Q²;

(d) lowercycloalkyl especially C₃₋₆ cycloalkyl, e.g., cyclopropyl, cyclopentyl and cyclohexyl;

(e) haloloweralkyl especially halo C₁₋₆ alkyl, e.g. CF₃—, CHF₂—, C₂F₅—;

(f) heteroaryl or heteroaryl substituted with X₅ and X₆ especially pyridyl, pyrryl, furyl or thienyl wherein X₅ and X₆ are as previously defined;

(g) benzyl or substituted benzyl of formula

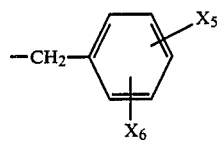

wherein X₅ and X₆ are as previously defined;

(h) loweralkynyl especially C₁₋₆ alkynyl such as —C≡CH; CH₃—C≡C—, or HC≡C—CH₂—;

(i) loweralkenyl especially C₁₋₆ alkenyl, such as CH₂=CH—, CH₃CH=CH—, CH₂=CHCH₂—, CH₃CH=CH—CH₂— or (CH₃)₂C=CH;

(j) phenylloweralkenyl of formula

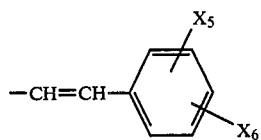

where X₅ and X₆ are as previously defined; or (k) phenylalkynyl of formula

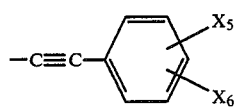

where X₅ and X₆ are as previously defined;

(l)

wherein R⁵ is R;

(m)

(n)

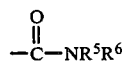

wherein R⁶ is R⁵ and can be the same as or different from R⁵;

(o)

(p)

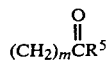

wherein m is 1 or 2;

(q) —(CH₂)ₘOR⁵;

(r)

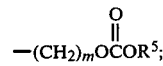

(s) —(CH₂)ₘNR⁵R⁶; or (t)

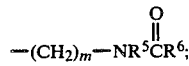

n is 0, 1 or 2; X₁, X₂, X₃ and X₄ independently are
(a) R as previously defined; or
(b) X₅.

Preferably, a 5-lipoxygenase inhibitor of this invention is of formula:

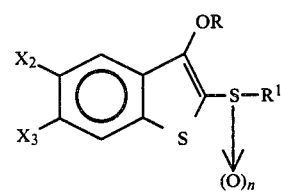

wherein X₂, X₃, R, R¹ and n are as previously defined.

More preferably, a 5-lipoxygenase inhibitor of this invention is of formula:

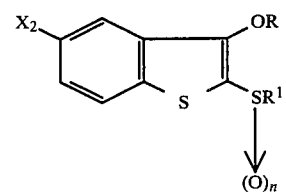

wherein X₂ is
(a) H;
(b) loweralkyl;
(c) haloloweralkyl especially halo-C₁₋₆alkyl such as CF₃; or
(d) loweralkenyl especially C₂₋₆alkenyl;

R is H, loweralkyl or C₁₋₆ alkyl —(CO)—; and R¹ is
(a) loweralkyl;
(b) phenyl or substituted phenyl;
(c) heteroaryl or substituted heteroaryl especially thienyl, furyl or pyrryl.

The representative compounds of the present invention are those listed in the following table:

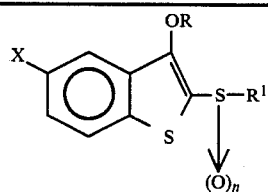

| R | R¹ | X | n | mp or M+ (m/e)[a] |
|---|---|---|---|---|
| H | Ph | H | 0 | 71-73° |
| φAc | Ph | H | 0 | 88-90° |
| H | Ph | Cl | 0 | 66-76° |
| φAc | Ph | Cl | 0 | 77-79° |
| H | Ph | SMe | 0 | M+ = 304 |
| φAc | Ph | SMe | 0 | 73-75° |
| H | Ph | H | 1 | M+ = 274 110 (dec) |
| H | Ph | CF₃ | 1 | M+ = 342 89 (dec) |
| H | NH(CH=C)Ph₂ | CF₃ | 2 | M+ = 475 |

M+ = molecular ion of a mass spectrum
Ac = acetyl; Ph = phenyl; and Me = methyl

B. Preparation of the compounds of the invention

The compounds of the present invention are prepared from known starting materials via various procedures, for example, methods as described below:

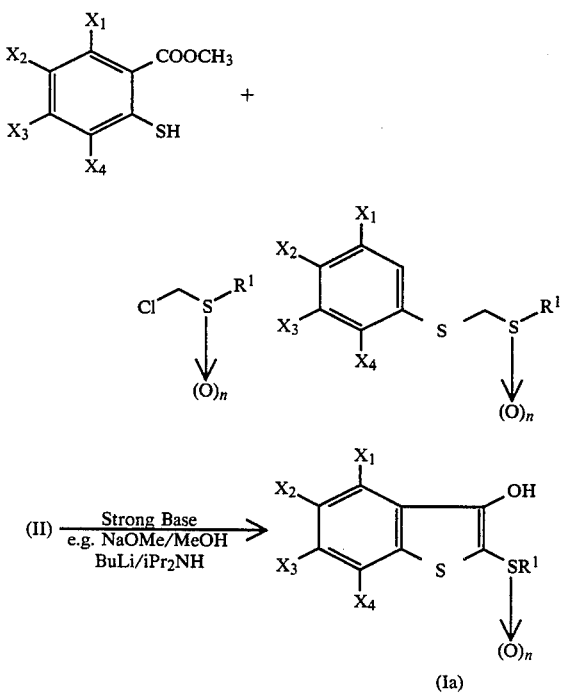

wherein X₁, X₂, X₃ and X₄, n, R¹ and R are as previously defined $$(Ia) \xrightarrow{\text{*appropriate modification}} (I)$$

*The appropriate modification includes common procedures for ether formation and acylation which are well known in the art. See Chapters 9 and 10, Compendium of Organic Synthetic Methods by Ion T. Harrison and Shayen Harrison, Wiley-Interscience, 1971 and references cited therein.

C. Utility of the compounds within the scope of the invention

This invention also relates to a method of treatment for patients (or mammalian animals raised in the dairy, meat, or fur industries or as pets) suffering from diseases mediated by leukotrienes and gastric irritation. More specifically, this invention is directed to a method of treatment involving the administration of one or more of the 5-lipoxygenase inhibitors of formula (I) as the active constituent.

Accordingly, a compound of Formula (I) can be used among other things to reduce inflammation, to relieve pain and fever associated with inflammation, to correct respiratory, cardiovascular, and intravascular alterations or disorders, and to regulate immediate hypersensitivity reactions that cause human asthma and allergic conditions.

For the treatment of inflammation, arthritis conditions, cardiovascular disorder, allergy, psoriasis, asthma, or other diseases mediated by leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
(a) a naturally-occurring phosphatide such as lecithin,
(b) a condensation product of an alkylene oxide with a fatty acid, for example, polyoxyethylene stearate,
(c) a condensation product of ethylene oxide with a long chain aliphatic alcohol, for example, heptadecaethyleneoxycetanol,
(d) a condensation product of ethylene oxide with a partial ester derived from a fatty acid and a hexitol such as polyoxyethylene sorbitol monooleate, or
(e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing one or more active compounds are employed.

Dosage levels of the order from about 0.1 mg to about 100 mg per kilogram of body weight per day are useful in the treatment of the above-indicated conditions (from about 5.0 mg to about 5 gms. per patients per day).

It would be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological Data Supporting the Utility of the Compound Within the Scope of the Invention The compounds of formula (I), e.g., 3-hydroxy-2-phenylsulfinylbenzo[b]thiophene (hereinafter referred to as compound A), are shown by the PAF assay described below as specific 5-lipoxygenase inhibitors useful in the treatment of leukotriene medicated diseases and as such can be effective cytoprotective agents useful in the prevention or treatment of gastric irritation and lesions.

Platelet Activating Factor Assay. (Induced Hyperalgesia in the Rat)

In this assay, which is sensitive to inhibition by lipoxygenase inhibitors but not cyclooxygenase inhibitors, compound A markedly reduced the response to PAF ($ED_{50}=0.3$ mg/kg p.o.). On the other hand, known cyclooxygenase inhibitors like Indomethacin, ibuprofen, piroxicam, and benoxaprofen were found to be completely ineffective in this assay.

Groups of 10 female Sprague-Dawley rats, 35–50 g (Taconic Farms), were fasted overnight prior to testing. Hyperalgesia was induced in the rat by the subplantar injection of 1 ug PAF in physiological saline. Pain threshold was measured by applying pressure to the plantar surface of the hindpaw by means of a compressed air driven piston with a 2 mm tip. Vocalization thresholds were obtained 3 hr after injection of the PAF. Compounds, prepared at various doses in 1% methylcellulose suspension, were administered perorally 30 minutes before PAF. For each drug treatment group, animals with response pressures in the inflamed paw of 200% of control was considered to be analgesic. The mean vocalization threshold for each group was also calculated. The $ED_{50}$ and 95% confidence limits were calculated by regression analysis.

The following examples illustrate the preparation of the compounds within the scope of the invention:

EXAMPLE 1

3-Acetoxy-2-phenylthiobenzo[b]thiophene

Step A: Preparation of methyl 2-phenylthiomethyl-thiobenzoate

A mixture of methyl o-mercaptobenzoate (3.36 g, 0.020 moles), chloromethylphenylsulfide (3.18 g, 0.020 moles) and sodium methoxide (1.40 g, 0.026 moles) in methanol (100 ml) was refluxed with stirring under nitrogen for 1 hour. The reaction was then cooled to 25° and cold water (125 ml) added. The product first oils out, but crystallizes after prolonged chilling at 0°. The product was filtered, water washed, taken up in methylene chloride, dried over MgSO$_4$ and evaporated to dryness under vacuum to give 5.36 g (92%) of methyl 2-phenythiomethylthiobenzoate as a white waxy solid, m.p. 70°–73°.

Step B: Preparation of 3-hydroxy-2-phenylthiobenzo[b]thiophene

To a three necked flask (flamed dried under dry nitrogen) was added 60 ml of dry tetrahydrofuran followed by 5.7 ml of isopropylamine (40.4 mM) and the solution cooled to 0° C. To this stirred solution added dropwise 27.6 ml of a 1.4 Molar solution of butyl lithium (38.7 mM) over 15 minutes. The solution was then cooled to $-60°$ C. and the methyl benzoate obtained in Step A (5.0 g; 17.2 mM) in 40 ml of THF was added dropwise over 30 minutes with rapid stirring. The solution was allowed to warm up to $+5°$ C. and stirred for 30 minutes. When TLC (3:1:2%)—Hexane:Et$_2$O:AcOH showed all the benzoate was consumed, reaction mixture was poured into water containing 2 to 4 equivalents of AcOH, extracted with CH$_2$Cl$_2$, dried over MgSO$_4$, filtered, and evaporated to give 5.11 g of brown oil which was chromatographed on a Silica Gel column in 20% EtOAc:Hexane to give 3.87 g crude product which was crystallized from hexane to give 2.73 g of 3-hydroxy-2-phenylthiobenzo[b]thiophene as pale pink crystals (61%), m.p. 71°–73° C.

Step C: Preparation of 3-acetoxy-2-phenylthiobenzo[b]thiophene

The 3-hydroxy compound was heated to 100° C. under nitrogen with 1.0 g of acetic anhydride for 30 minutes and cooled under nitrogen stream to remove excess acetic anhydride. The solid residue was crystallized in 5 ml of hexane to give a 79% yield of 3-acetoxy-2-phenylthiobenzo[b]thiophene as pink crystals, m.p. 88°–90° C.

EXAMPLE 2

3-Hydroxy-2-phenylsulfonyl-5-trifluoro-methylbenzo[b]thiophene

Step A: Preparation of methyl 2-phenylsulfonylmethylthio-5-trifluoromethylbenzoate A mixture of methyl 2-mercapto-5-trifluoromethylbenzoate (0.94 g, 0.0040 moles), chloromethylphenylsulfoxide (0.70 g, 0.0040 moles) and K$_2$CO$_3$ (1.66 g, 0.012 moles) in DMF (10 ml) was stirred vigorously at 50° for 45 minutes. The reaction was cooled, diluted with water (30 ml), and the resulting precipitate collected, water and hexane washed, and dried under vacuum to afford 1.05 g (70%) of methyl 2-phenylsulfonylmethylthio-5-trifluoromethylbenzoate. R$_f$ (Et$_2$O:Hexane, 1:1+1% Acetic Acid)=0.15.

Step B: Preparation of 3-hydroxy-2-phenylsulfonyl-5-trifluoromethylbenzo[b]thiophene Sodium methoxide (0.43 g, 0.0080 moles) was added to a nitrogen purged flask containing the thiosulfoxide ester, I (1.00 g, 0.00267 moles) in methanol (12 ml), and the mixture was refluxed for 5 minutes. The reaction was cooled to RT and neutralized with concentrated HCl (0.80 g) in water (12 ml). After cooling for 1 hour at 0°, the precipitate was collected, washed with 50% methanol and hexane, and dried under vacuum to afford 0.88 g (97%) of 3-hydroxy-2-phenylsulfonyl-5-trifluoromethylbenzo[b]thiophene.

What is claimed is:

1. A compound of formula:

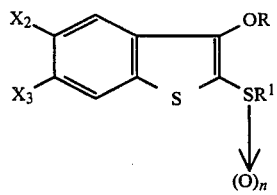

wherein X$_2$ and X$_3$ independently are
(a) H;
(b) loweralkyl;
(c) haloloweralkyl; or
(d) loweralkenyl;
R is H, C$_{1-6}$ or C$_{1-6}$alkyl—CO—; and R$^1$ is
(a) C$_{1-6}$alkyl
(b) phenyl or substituted phenyl of formula

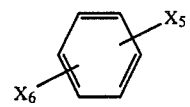

wherein X$_5$ and X$_6$ independently are:
(1) Q, where Q is H, loweralkyl, halolowerlalkyl, phenyl or naphthyl;
(2) halo;
(3) loweralkenyl;
(4) loweralkynyl;
(5) —SQ;
(6) —OQ;
(7) —CHQCOQ$^1$, where Q is Q$^1$ and can be the same as or different from Q$^1$;
(8) —CHQCOOQ$^1$;
(9) —CH$_2$SQ or —CHQSQ$^1$;
(10) —CH$_2$OQ or —CHQOQ$^1$;
(11) —COQ;
(12) —COOQ;
(13) —OCOQ;
(14) —NQQ$^1$;
(15) —NQCOQ$^1$;
(16) —NQSO$_2$Q$^1$;
(17) —SO$_2$NQQ$^1$;
(18) —SOQ;
(19) —SO$_2$Q;
(20) —SO$_3$Q;
(21) —CN;
(22) —NO$_2$;
(23) —CONQQ$^1$;
(24) —NO;
(25) —CSQ;
(26) —CSNQQ$^1$;

(27) —CF₂SQ;
(28) —CF₂OQ;
(29) —NQCONQ¹Q² wherein Q² is Q or Q¹ and can be the same or different from either of Q or Q¹;
(c) heteroaryl selected from a group consisting of thienyl, furyl, pyrryl and pyridyl, said group being substituted with X₅ and X₆;
(d) NH(CH=C)Ph₂ wherein Ph is phenyl; and
n is 0, 1 or 2.

2. The compound of claim 1 which is of formula

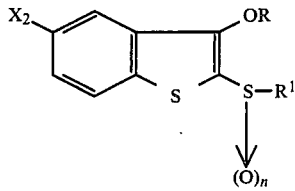

wherein R, R¹, X₂ and n are as defined in the following table:

| R | R¹ | X₂ | n |
|---|----|----|---|
| H | Ph | H | 0 |
| Ac | Ph | H | 0 |
| H | Ph | Cl | 0 |
| Ac | Ph | Cl | 0 |
| H | Ph | SMe | 0 |
| Ac | Ph | SMe | 0 |
| H | Ph | H | 1 |
| H | Ph | CF₃ | 1 |
| H | NH(CH=C)Ph₂ | CF₃ | 2 | wherein Ph is phenyl, Ac is acetyl and Me is methyl.

3. The compound of claim 1 which is
(a) 3-hydroxy-2-phenylsulfinylbenzo[b]thiophene; or
(b) 3-hydroxy-2-phenylsulfonyl-5-trifluoromethylbenzo[b]thiophene.

4. A pharmaceutical composition for treating leukotrienes-mediated diseases which cause inflammation and pain in mammalian species comprising a pharmaceutically acceptable carrier and an effective amount of a compound of formula:

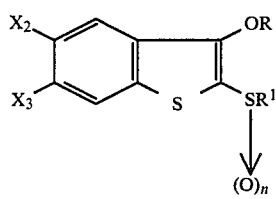

wherein X₂ and X₃ independently are
(a) H;
(b) loweralkyl;
(c) haloloweralkyl; or
(d) loweralkenyl;
R is H, C₁₋₆ or C₁₋₆alkyl—CO—; and R¹ is
(a) C₁₋₆alkyl (b) phenyl or substituted phenyl of formula

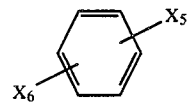

wherein X₅ and X₆ independently are:
(1) Q, where Q is H, loweralkyl, halolowerlakyl, phenyl or naphthyl;
(2) halo;
(3) loweralkenyl;
(4) loweralkynyl;
(5) —SQ;
(6) —OQ;
(7) —CHQCOQ¹, where Q is Q¹ and can be the same as or different from Q¹;
(8) —CHQCOOQ¹;
(9) —CH₂SQ or —CHQSQ¹;
(10) —CH₂OQ or —CHQOQ¹;
(11) —COQ;
(12) —COOQ;
(13) —OCOQ;
(14) —NQQ¹;
(15) —NQCOQ¹;
(16) —NQSO₂Q¹;
(17) —SO₂NQQ¹;
(18) —SOQ;
(19) —SO₂Q;
(20) —SO₃Q;
(21) —CN;
(22) —NO₂;
(23) —CONQQ¹;
(24) —NO;
(25) —CSQ;
(26) —CSNQQ¹;
(27) —CF₂SQ;
(28) —CF₂OQ;
(29) —NQCONQ¹Q² wherein Q² is Q or Q¹ and can be the same or different from either of Q or Q¹;
(c) heteroaryl selected from a group consisting of thienyl, furyl, pyrryl and pyridyl, said group being substituted with X₅ and X₆;
(d) NH(CH=C)Ph₂ wherein Ph is phenyl; and
n is 0, 1 or 2.

5. The composition of claim 4 wherein the active compound is of formula:

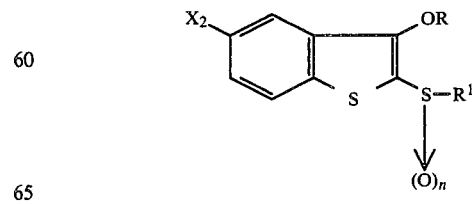

wherein R, R¹, X₂ and n are as defined in the following table:

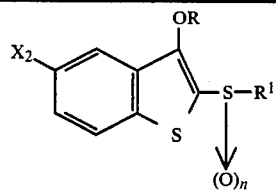

| R  | R¹         | X₂   | n |
|----|------------|------|---|
| H  | Ph         | H    | 0 |
| Ac | Ph         | H    | 0 |
| H  | Ph         | Cl   | 0 |
| Ac | Ph         | Cl   | 0 |
| H  | Ph         | SMe  | 0 |
| Ac | Ph         | SMe  | 0 |
| H  | Ph         | H    | 1 |
| H  | Ph         | CF₃  | 1 |
| H  | NH(CH=C)Ph₂| CF₃  | 2 | wherein Ph is phenyl, Ac is acetyl and Me is methyl.

6. The composition of claim 4 wherein the active compound is
(a) 3-hydroxy-2-phenylsulfinylbenzo[b]thiophene; or
(b) 3-hydroxy-2-phenylsulfonyl-5-trifluoromethylbenzo[b]thiophene.

7. A method for the treatment of leukotrienes-mediated diseases which cause inflammation and pain comprising the administration to a mammalian species in need of such treatment a therapeutically effective amount of a compound of formula

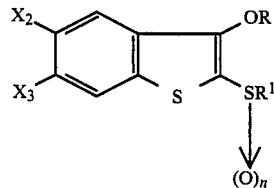

wherein X₂ and X₃ independently are
(a) H;
(b) loweralkyl;
(c) haloloweralkyl; or
(d) loweralkenyl;
R is H, $C_{1-6}$ or $C_{1-6}$alkyl—CO—; and R¹ is
(a) $C_{1-6}$alkyl
(b) phenyl or substituted phenyl of formula

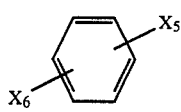

wherein X₅ and X₆ independently are:
(1) Q, where Q is H, loweralkyl, haloloweralkyl, phenyl or naphthyl;
(2) halo;
(3) loweralkenyl;
(4) loweralkynyl;
(5) —SQ;
(6) —OQ;
(7) —CHQCOQ¹, where Q is Q¹ and can be the same as or different from Q¹;
(8) —CHQCOOQ¹;
(9) —CH₂SQ or —CHQSQ¹;
(10) —CH₂OQ or —CHQOQ¹;
(11) —COQ;
(12) —COOQ;
(13) —OCOQ;
(14) —NQQ¹;
(15) —NQCOQ¹;
(16) —NQSO₂Q¹;
(17) —SO₂NQQ¹;
(18) —SOQ;
(19) —SO₂Q;
(20) —SO₃Q;
(21) —CN;
(22) —NO₂;
(23) —CONQQ¹;
(24) —NO;
(25) —CSQ;
(26) —CSNQQ¹;
(27) —CF₂SQ;
(28) —CF₂OQ;
(29) —NQCONQ¹Q² wherein Q² is Q or Q¹ and can be the same or different from either of Q or Q¹;
(c) heteroaryl selected from a group consisting of thienyl, furyl, pyrryl and pyridyl, said group being substituted with X₅ and X₆;
(d) NH(CH=C)Ph₂ wherein Ph is phenyl; and
n is 0, 1 or 2.

8. The method of claim 7 wherein the active compound is of formula:

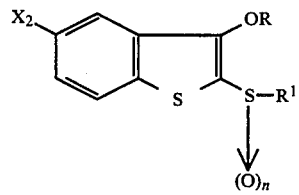

wherein R, R¹, X₂ and n are as defined in the following table:

| R  | R¹         | X₂   | n |
|----|------------|------|---|
| H  | Ph         | H    | 0 |
| Ac | Ph         | H    | 0 |
| H  | Ph         | Cl   | 0 |
| Ac | Ph         | Cl   | 0 |
| H  | Ph         | SMe  | 0 |
| Ac | Ph         | SMe  | 0 |
| H  | Ph         | H    | 1 |
| H  | Ph         | CF₃  | 1 |
| H  | NH(CH=C)Ph₂| CF₃  | 2 | wherein Ph is phenyl, Ac is acetyl and Me is methyl.

9. The method of claim 7 wherein the active compound is
(a) 3-hydroxy-2-phenylsulfinylbenzo[b]thiophene; or
(b) 3-hydroxy-2-phenylsulfonyl-5-trifluoromethylbenzo[b]thiophene.

* * * * *